United States Patent [19]

Dautzenberg et al.

[11] 4,291,182

[45] Sep. 22, 1981

[54] PROCESS FOR THE PREPARATION OF AROMATIC HYDROCARBONS AND HYDROGEN FROM BUTANE

[75] Inventors: Frits M. Dautzenberg; Nigel Wagstaff, both of Amsterdam, Netherlands

[73] Assignee: Shell Oil Company, Houston, Tex.

[21] Appl. No.: 129,446

[22] Filed: Mar. 11, 1980

[30] Foreign Application Priority Data

Mar. 14, 1979 [NL] Netherlands .......................... 7902018

[51] Int. Cl.$^3$ .......................... C07C 2/76; C07C 15/02
[52] U.S. Cl. ...................................... 585/415; 208/135
[58] Field of Search .......................... 585/415; 208/135

[56] References Cited

U.S. PATENT DOCUMENTS

| | | | |
|---|---|---|---|
| 3,760,024 | 9/1973 | Cattanach | 585/415 |
| 3,775,501 | 11/1973 | Kaeding et al. | 585/414 |
| 3,845,150 | 10/1974 | Yan et al. | 208/135 |
| 4,180,689 | 12/1979 | Davies et al. | 585/407 |

*Primary Examiner*—Delbert E. Gantz
*Assistant Examiner*—G. E. Schmitkons
*Attorney, Agent, or Firm*—Ronald R. Reper

[57] ABSTRACT

A process is disclosed for the conversion of a hydrocarbon stream which is primarily $C_4$ paraffins to aromatic hydrocarbons and hydrogen over certain crystalline silicates containing zinc.

5 Claims, No Drawings

PROCESS FOR THE PREPARATION OF AROMATIC HYDROCARBONS AND HYDROGEN FROM BUTANE

BACKGROUND OF THE INVENTION

The invention relates to a process for the preparation of aromatic hydrocarbons and hydrogen from a paraffin with four carbon atoms in the molecule (a $C_4$ paraffin) or from a hydrocarbon mixture which consists of more than 75% w paraffins with at most four carbon atoms in the molecule ($C_{4-}$ paraffins) and more than 50% w $C_4$ paraffins, using a crystalline silicate as the catalyst.

In an investigation by Applicants concerning the abovementioned process it has been found that the activity, the aromatics selectivity and the hydrogen selectivity of these crystalline silicate catalysts are greatly dependent on the value of y in the formula which gives the overall composition of the silicate, are further dependent on the metal promoter which has been deposited on the silicate and are dependent upon the pressure used in the process. It was found that to reach an activity, an aromatics selectivity and a hydrogen selectivity which are acceptable for commercial use of the process, y should be at most 0.01, the silicate should contain zinc as the promoter and the process should be carried out at a pressure below 5 bar.

SUMMARY OF THE INVENTION

The present invention therefore relates to a process for the preparation of aromatic hydrocarbons and hydrogen, in which a $C_4$ paraffin or a hydrocarbon mixture which consists of more than 75% w $C_{4-}$ paraffins and more than 50% w $C_4$ paraffins, is contacted with a crystalline silicate as defined above as the catalyst at a pressure below 5 bar, in which the value of y in the formula which gives the overall composition of the silicate is at most 0.01 and the silicate contains zinc as the promoter.

DESCRIPTION OF PREFERRED EMBODIMENTS

In the process according to the invention the hydrocarbon feed starting material should be a $C_4$ paraffin or a hydrocarbon mixture which consists of more than 75% w $C_{4-}$ paraffins and more than 50% w $C_{4-}$ paraffins. Eligible $C_{4-}$ paraffins are methane, ethane, propane, butane and isobutane. If the starting material is a hydrocarbon mixture which comprises in addition to one or more $C_{4-}$ paraffins one or more other hydrocarbons, among these other hydrocarbons may be monoolefins, diolefins or $C_5{}^+$ paraffins. The preferred starting material is a hydrocarbon mixture consisting of more than 75% w $C_4$ paraffins. A very suitable feed for the present process is a hydrocarbon mixture consisting substantially of $C_3$ and $C_4$ paraffins which has been obtained as by-product in mineral oil production.

The process according to the invention is carried out at an elevated temperature, preferably at a temperature of from 350° to 700° C., and particularly of from 400° to 600° C., a pressure of from 1 to 3 bar and a space velocity of from 0.1 to 20 g.g$^{-1}$.h$^{-1}$ and particularly of from 0.5 to 10 g.g$^{-1}$.h$^{-1}$.

In the process according to the invention a $C_4$ paraffin or a hydrocarbon mixture which consists of more than 75% w $C_4{}^-$ paraffins and more than 50% w $C_4$ paraffins, is converted into aromatic hydrocarbons and hydrogen by contacting this feed with certain crystalline silicates. The crystalline silicates are characterized in that they have the following properties after 1 hour's calcining in air at 500° C.

(a) thermally stable up to a temperature above 600° C., (b) an X-ray powder diffraction pattern showing, inter alia, the reflections given in Table A.

TABLE A

| Radiation: Cu-K<br>2 θ | Wavelength 0.15418 nm<br>relative intensity |
|---|---|
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | wherein the letters used have the following meanings:
VS = very strong;
S = strong;
M = moderate;
W = weak;
θ = angle according to Bragg's law, (c) after conversion of the silicate into the H-form and after evacuation at $2 \times 10^{-9}$ bar and 400° C. for 16 hours and measured at a hydrocarbon pressure of $8 \times 10^{-2}$ bar and 100° C., the adsorption of n-hexane is at least 0.8 mmol/g, the adsorption of 2,2-dimethylbutane at least 0.5 mmol/g and the ratio $$\frac{\text{absorption of n-hexane}}{\text{absorption of 2,2-dimethylbutane}} \text{ at least } 1.5,$$

(d) the composition, expressed in moles of the oxides, is as follows:

$$y(1.0 \pm 0.3)M_{n/2}O.y.Al_2O_3.SiO_2$$

wherein M=H and/or alkali metal and/or alkaline-earth metal, n is the valency of M and $0 < y \leq 0.01$.

For the adsorption measurements mentioned under (c) the silicate should first be converted into the H-form. This conversion is effected by boiling the silicate calcined at 500° C. with 1.0 molar $NH_4NO_3$ solution, washing with water, boiling again with 1.0 molar $NH_4NO_3$ solution and washing, drying at 120° C. and calcining at 500° C.

The complete X-ray powder diffraction pattern of a typical example of a silicate eligible for use according to the invention is shown in Table B (radiation: Cu-K; wavelength: 0.15418 nm).

TABLE B

| 2θ | relative intensity<br>(100. I/I$_o$) | description |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |

TABLE B-continued

| 2θ | relative intensity (100. I/I₀) | description |
|---|---|---|
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100* | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

*$I_o$ = intensity of the strongest separate reflection present in the pattern.

The letters used in Table B for describing the reflections have the following meanings:

SP = sharp;  SR = shoulder;  NL = normal; BD = broad; θ = angle according to Bragg's law.

The crystalline silicates which are used as the catalyst in the process according to the invention can be prepared from an aqueous mixture as the starting material which contains the following compounds: one or more compounds of an alkali- or alkaline-earth metal (M), one or more compounds containing an organic cation (R) or from which such a cation is formed during the preparation of the silicate, one or more silicon compounds and one or more aluminium compounds. Exemplary organic cations include, e.g., primary, secondary and tertiary alkyl amines and quaternary ammonium compounds. The preparation is performed by maintaining the mixture at elevated temperature until the silicate has been formed and subsequently separating the crystals of the silicate from the mother liquor. In the aqueous mixture from which the silicates are prepared the various compounds should be present in the following ratios, expressed in moles of the oxides:

$M_{2/n}O:(R)_{2/p}O = 0.1-20$, $(R)_{2/p}O:SiO_2 = 0.01-0.5$, $SiO_2:Al_2O_3 \geq 100$, and $H_2O:SiO_2 = 5-50$;

n is the valency of M and p is the valency of R.

In the preparation of the silicates it is preferred to start from a basic mixture in which M is present in a sodium compound and R in a tetrapropylammonium compound.

For the silicates which are suitable for use as the catalyst in the process according to the invention holds: $0 < y \leq 0.01$. Preference is given to the use of silicates with y > 0.0017 and in particular with y > 0.0022. Further, preference is given to silicates with y < 0.0065.

The value of y in the formula which gives the composition of the silicates can be adjusted with the aid of the molar ratio of $SiO_2$ to $Al_2O_3$ in the starting mixture, in the sense that silicates with a lower value for y are obtained according as the molar ratio of $SiO_2$ to $Al_2O_3$ in the starting mixture is chosen higher.

The silicates prepared as described above contain alkali metal ions and/or alkaline-earth metal ions and organic cations. When suitable exchange methods are used, the alkali metal ions and alkaline-earth metal ions can be replaced by other cations, such as hydrogen ions or ammonium ions. Organic cations can very conveniently be converted into hydrogen ions by calcining the silicates. The crystalline silicates which are used as the catalysts in the process according to the invention preferably have an alkali metal content of less than 0.1% w, and particularly less than 0.01% w. When the crystalline silicates are used as the catalyst, they may, if desired, be combined with a natural or synthetic binder material such as bentonite or kaolin.

In the process according to the invention a silicate should be used which has zinc as the promoter. A preferred silicate is one which contains 0.05 to 20% w and particularly 0.1 to 5% w zinc. The incorporation of the zinc into the silicate may be performed in various ways, for instance by ion exchange or by impregnation with a solution of one or more zinc salts, e.g., nitrates, acetates etc. In the process of this invention it is preferred to use a silicate in which the zinc incorporation was performed by impregnating the silicate with an aqueous solution of a zinc salt followed by drying and calcining of the impregnated material. Preferably this zinc is in the oxide form.

The process according to the invention can very conveniently be carried out by conducting the feed in upward or downward direction through a vertically mounted reactor, in which a fixed or moving bed of the catalyst concerned is present.

The invention will now be explained with reference to the following example.

EXAMPLE

Four crystalline silicates (silicates A-D) were prepared by heating mixtures of $SiO_2$, $NaAlO_2$, NaOH and $[(C_3H_7)_4N]OH$ in water in an autoclave under autogenous pressure of 24 hours at 150° C. After the reaction mixtures had cooled down, the silicates formed were filtered off, washed with water until the pH of the wash water was about 8 and dried for two hours at 120° C. After 1 hour's calcining in air at 500° C. the silicates A-D had the following properties:

(a) thermally stable up to a temperature above 800° C.;

(b) an X-ray powder diffraction pattern substantially equal to the one given in Table B;

(c) after conversion of the silicate into the H-form and after evacuation at $2 \times 10^{-9}$ bar and 400° C. for 16 hours and measured at a hydrocarbon pressure of $8 \times 10^{-2}$ bar and 100° C., the adsorption of n-hexane is 1.2 mmol/g, the adsorption of 2,2-dimethylbutane 0.7 mmol/g and the ratio $$\frac{\text{adsorption of n-hexane}}{\text{adsorption of 2,3-dimethylbutane}} = 1.7$$

(d) the composition, expressed in moles of the oxides, is the following:

silicate A: 0.0038 $M_2O$. 0.0038 $Al_2O_3.SiO_2$
silicate B: 0.0077 $M_2O$. 0.0077 $Al_2O_3.SiO_2$
silicate C: 0.026 $M_2O$. 0.026 $Al_2O_3.SiO_2$
silicate D: 0.0059 $M_2O$. 0.0059 $Al_2O_3.SiO_2$ wherein M=H and Na.

The molar composition of the aqueous mixtures from which the silicates A-D were prepared are given in Table C.

TABLE C

| Silicate | A | B | C | D |
|---|---|---|---|---|
| Na$_2$O | 16 | 8 | 1.5 | 8 |
| Al$_2$O$_3$ | 1 | 1 | 1 | 1 |
| [(C$_3$H$_7$)$_4$N]$_2$O | 72 | 36 | 2.25 | 12 |
| SiO$_2$ | 400 | 200 | 37.5 | 200 |
| H$_2$O | 7200 | 3600 | 675 | 3000 |

The silicates I-IV were prepared from the silicates A-D, respectively, by boiling the materials calcined at 500° C. with 1.0 molar NH$_4$NO$_3$ solution, washing with water, boiling again with 1.0 molar NH$_4$NO$_3$ solution and washing, drying at 120° C. and calcining at 500° C.

From the silicates I-IV as the starting materials the silicates 1-7 were prepared, which contained one of the following elements: zinc, tungsten, gallium and manganese. The preparation was effected by impregnating samples of the silicates I-IV with an aqueous solution of a salt of the element concerned, followed by drying and calcining of the impregnated material.

The silicates 1-7 had the following compositions:
Silicate 1: 2% w Zn on silicate I
Silicate 2: 2% w Zn on silicate II
Silicate 3: 2% w Zn on silicate III
Silicate 4: 2% w W on silicate IV
Silicate 5: 2% w Ga on silicate IV
Silicate 6: 3% w Mn on silicate III
Silicate 7: 0.1% w Zn on silicate I The silicates 1-7 and silicate IV were tested as the catalyst for the preparation of aromatic hydrocarbons and hydrogen from a C$_4$ paraffin. The test was carried out in a 50-ml reactor fitted with a fixed catalyst bed having a volume of 5 ml and comprising the silicate concerned. The C$_4$ paraffin was conducted over the catalyst at a temperature of 475° C. and a space velocity of 2 g C$_4$ paraffin/g silicate/h. The results of these experiments are given in Table D. The following data are included in the table:

(a) the activity =
$$\frac{pbw \text{ (total product } - C_4 \text{ hydrocarbons in product)}}{pbw \text{ total product}} \times 100$$

(b) the aromatics selectivity =
$$\frac{pbw \text{ aromatic hydrocarbons in product}}{pbw \text{ (total product } - C_4 \text{ hydrocarbons in product)}} \times 100$$

(c) the hydrogen selectivity =
$$\frac{pbw \text{ hydrogen in product}}{pbw \text{ (total product } - C_4 \text{ hydrocarbons in product)}} \times 100$$

(d) the C$_4$ paraffin used as the feed, and
(e) the pressure used.

TABLE D

| Exp. No. | Silicate Number | Feed | Pressure, bar | Activity | Aromatics selectivity | Hydrogen selectivity |
|---|---|---|---|---|---|---|
| 1 | 1 | isobutane | 1.5 | 79.9 | 41.3 | 3.63 |
| 2 | 2 | isobutane | 1.5 | 93.6 | 38.0 | 2.62 |
| 3 | 3 | isobutane | 1.5 | 97.5 | 37.2 | 2.05 |
| 4 | IV | isobutane | 1.5 | 23.1 | 2.81 | 3.20 |
| 5 | 4 | isobutane | 1.5 | 25.0 | 13.6 | 3.20 |
| 6 | 5 | isobutane | 1.5 | 15.0 | 11.1 | 5.53 |
| 7 | 6 | isobutane | 1.5 | 53.3 | 14.2 | 1.69 |
| 8 | 7 | isobutane | 1.5 | 42.0 | 41.0 | 3.81 |
| 9 | 7 | isobutane | 10 | 68.2 | 27.9 | 1.61 |
| 10 | 1 | n-butane | 1.5 | 61.6 | 42.3 | 3.73 |

Of the experiments shown in Table D only the numbers 1, 2, 8 and 10 are experiments according to the invention. These experiments were carried out at a pressure lower than 5 bar using as the catalysts silicates which contained zinc as the promoter and which had the required y. In these experiments both a high activity and a high aromatics selectivity and hydrogen selectivity were reached. The experiments 3-7 and 9 are outside the scope of the invention and have been included for comparison. In experiment 3 a silicate with too high y-value was used, which led to an unacceptably low hydrogen selectivity. In the experiments 4-6, silicates were used which had either no promoter, or a promoter other than zinc, which led to an unacceptably low activity and aromatics selectivity. In experiment 7 a silicate with too high y-value and with a promoter other than zinc was used and in experiment 9 too high a pressure was used, which resulted in both cases in an unacceptably low aromatics selectivity and hydrogen selectivity.

What is claimed is:

1. A process for the preparation of aromatic hydrocarbons and hydrogen, which comprises contacting in a contact zone as feed a C$_4$ paraffin or a hydrocarbon mixture which consists of more than 75% w C$_{4-}$ paraffins and more than 50% w C$_4$ paraffins with a catalyst consisting essentially of a zinc-promoted crystalline silicate at a temperature of from 350° to 700° C., a space velocity of from 0.1 to 20 g.g$^{-1}$.h$^{-1}$ and at a pressure below 5 bar, which silicate is characterized as having the following properties after 1 hour's calcining in air at 500° C.:

(a) thermally stable up to a temperature above 600° C., (b) an X-ray powder diffraction pattern showing, inter alia, the reflections given in Table A.

TABLE A

| Radiation: Cu-K 2 $\theta$ | Wavelength 0.15418 nm relative intensity |
|---|---|
| 7.8-8.2 | S |
| 8.7-9.1 | M |
| 11.8-12.1 | W |
| 12.4-12.7 | W |
| 14.6-14.9 | W |
| 15.4-15.7 | W |
| 15.8-16.1 | W |
| 17.6-17.9 | W |
| 19.2-19.5 | W |
| 20.2-20.6 | W |
| 20.7-21.1 | W |
| 23.1-23.4 | VS |
| 23.8-24.1 | VS |
| 24.2-24.8 | S |
| 29.7-30.1 | M | wherein the letters used have the following meanings:
VS = very strong;
S = strong;
M = moderate;
W = weak;
$\theta$ = angle according to Bragg's law, (c) after conversion of the silcate into the H-form and after evacuation at $2 \times 10^{-9}$ bar and 400° C. for 16 hours and measured at a hydrocarbon pressure of $8 \times 10^{-2}$ bar and 100° C., the adsorption of n-hexane is at least 0.8 mmol/g, the adsorption of 2,2-dimethylbutane at least 0.5 mmol/g and the ratio $$\frac{\text{absorption of n-hexane}}{\text{absorption of 2,2-dimethylbutane}} \text{ at least 1.5,}$$

(d) the composition, expressed in moles of the oxides, is as follows:

$$y(1.0 \pm 0.3)M_{n/2}O \cdot y \cdot Al_2O_3 \cdot SiO_2$$

wherein M=H and/or alkali metal and/or alkaline-earth metal, n is the valency of M and $0.0065 < y \leq 0.0017$; said catalyst containing 0.05 to 20% w zinc and withdrawing an aromatic hydrocarbon mixture and a hydrogen-containing gaseous mixture from said contact zone.

2. A process according to claim 1, wherein said feed is a hydrocarbon mixture which consists of more than 75% w $C_4$ paraffins.

3. A process according to claim 1, wherein said feed is a hydrocarbon mixture consisting substantially of $C_3$ and $C_4$ paraffins.

4. A process according to claim 1, wherein said contacting is carried out at a temperature of from 400° to 600° C., a pressure of from 1 to 3 bar and a space velocity of from 0.5 to 10 $g \cdot g^{-1} \cdot h^{-1}$.

5. A process according to claim 1, wherein the silicate catalyst contains 0.1 to 5% w zinc.

* * * * *